United States Patent [19]

Immel et al.

[11] Patent Number: 4,952,549
[45] Date of Patent: Aug. 28, 1990

[54] RUTHENIUM CATALYST, PROCESS FOR ITS PREPARATION AND PROCESS FOR THE PREPARATION OF A MIXTURE OF CYCLOHEXYLAMINE AND DICYCLOHEXYLAMINE USING THE RUTHENIUM CATALYST

[75] Inventors: Otto Immel; Hans-Helmut Schwarz, both of Krefeld, Fed. Rep. of Germany

[73] Assignee: Bayer Aktiengesellschaft, Leverkusen, Fed. Rep. of Germany

[21] Appl. No.: 295,319

[22] Filed: Jan. 10, 1989

[30] Foreign Application Priority Data

Jan. 22, 1988 [DE] Fed. Rep. of Germany ....... 3801756

[51] Int. Cl.$^5$ .................... B01J 23/56; B01J 23/58; C07C 85/24; C07C 87/36
[52] U.S. Cl. .................... 502/330; 502/332; 502/333; 502/334; 502/344; 564/450; 564/462
[58] Field of Search ............ 502/313, 330, 332, 333, 502/334, 344, 184, 243; 564/450, 462

[56] References Cited

U.S. PATENT DOCUMENTS

| | | | |
|---|---|---|---|
| 2,184,070 | 12/1939 | Bertsch | 564/450 |
| 3,196,179 | 7/1965 | Robinson | 564/450 |
| 3,636,108 | 1/1972 | Brake | 564/450 |
| 3,655,747 | 4/1972 | Sennewald et al. | 502/313 |
| 3,697,449 | 10/1972 | Loren . | |
| 3,846,343 | 11/1974 | Erickson et al. | 502/334 |
| 4,049,584 | 9/1977 | Weissel | 564/450 |
| 4,070,399 | 1/1978 | Butte, Jr. . | |
| 4,186,145 | 1/1980 | Weissel | 564/450 |
| 4,496,666 | 1/1985 | Pesa et al. . | |

FOREIGN PATENT DOCUMENTS 1106319 5/1961 Fed. Rep. of Germany .
0969542 9/1964 United Kingdom .
2023020 12/1979 United Kingdom .

OTHER PUBLICATIONS

Chemical Abstracts, Band 85, Nr. 23, 6, Dezember 1976, Zusammenfassung Nr. 176953g, Columbus, Ohio, U.S.; & SU-A-520 346 (All Union Scientific-Research and Design Intitute of Monomers), 05-07-1976, *Zusammenfassung*.

Primary Examiner—H. M. S. Sneed
Assistant Examiner—J. Saba
Attorney, Agent, or Firm—Sprung Horn Kramer & Woods

[57] ABSTRACT

Substituted or unsubstituted cyclohexylamine and substituted or substituted dicyclohexylamine can be produced by catalytic hydrogenation of substituted or unsubstituted aniline, for which a catalyst is used containing ruthenium and palladium which are attached to a support and which catalyst furthermore contains a basic alkali metal compound. The catalyst contains the noble metals in a total amount of 0.05 to 5% by weight and in a weight ratio of ruthenium to palladium such as 1:9–9:1. The basic alkali metal compound is present in an amount of 0.1–10% by weight. All percentages are based on the total weight of the catalyst.

17 Claims, No Drawings

RUTHENIUM CATALYST, PROCESS FOR ITS PREPARATION AND PROCESS FOR THE PREPARATION OF A MIXTURE OF CYCLOHEXYLAMINE AND DICYCLOHEXYLAMINE USING THE RUTHENIUM CATALYST

BACKGROUND OF THE INVENTION

The invention relates to a supported catalyst containing ruthenium and palladium, to a process for the preparation of such a catalyst and to a process for the preparation of a mixture of substituted or unsubstituted cyclohexylamine and substituted or unsubstituted dicyclohexylamine by catalytic hydrogenation of substituted or unsubstituted aniline using this ruthenium catalyst.

It is known to prepare cyclohexylamine and other ring-hydrogenated amino compounds by catalytic hydrogenation of aniline and other aromatic amino compounds. The known catalysts for this reaction are: cobalt catalysts containing a basic additive (GB 969,542), Raney cobalt (JP 68/03180), ruthenium catalysts (DE-AS (German Published Specification) 1,106,319), ruthenium catalysts doped with alkali metal compounds (U.S. Pat. No. 3,636,108) or nickel catalysts (German Patent Specification No. 805,518).

The majority of the processes mentioned are carried out under pressure and mainly produce cyclohexylamine along with only a small amount of dicyclohexylamine. Dicyclohexylamine is therefore often prepared by other processes, for example by hydrogenation of diphenylamine under pressure using a ruthenium catalyst (DE-AS (German Published Specification) 1,106,319). Furthermore, dicyclohexylamine is formed in the reaction of cyclohexanone with cyclohexylamine in the presence of a palladium/carbon catalyst at a hydrogen pressure of about 4 bar (FR 1,333,692). The process of German Patent Specification No. 805,518 mentioned is mainly aimed at the production of dicyclohexylamine, although it involves complex recycling of byproducts.

Further drawbacks of the processes mentioned are the in some cases significant amounts of cyclohexane waste product and also the short life of the catalysts used. It was therefore desired to develop a process which is useful on an industrial scale and in which the loss caused by the formation of cyclohexane are reduced and the life of the catalyst used is improved and also to develop a process in which cyclohexylamine and dicyclohexylamine are formed together in amounts which, depending on the demand of the two substances mentioned, are variable.

SUMMARY OF THE INVENTION

Surprisingly it has been found that the requirements mentioned are met by the use of the ruthenium supported catalysts characterized below.

Accordingly, the invention relates to catalysts containing ruthenium and palladium on a support containing the noble metals in a total amount of 0.05 to 5% by weight, preferably 0.1-4% by weight, particularly preferably 0.1-3% by weight and in a weight ratio of ruthenium to palladium such as 1:9-9:1, preferably 2:8-8:2, particularly preferably 3:7-7:3, which catalysts furthermore contain 0.1-10% by weight, preferably 0.2-5% by weight, of a basic alkali metal compound, all percentages being based on the total weight of the catalyst.

DETAILED DESCRIPTION OF THE INVENTION

Accordingly, the catalysts according to the invention are mainly distinguished by the combination of ruthenium with palladium. Compared to the catalysts containing only ruthenium, such catalysts have a significantly higher life, which is indispensible for their use in an industrial process.

Examples of basic alkali metal compounds for the catalysts according to the invention are the oxides, hydroxides, alcoholates or salts of weak acids of lithium, sodium, potassium, rubidium or caesium, preferably of sodium or potassium. Weak acids are for example carbonic acid, acetic acid, formic acid and other carboxylic acids whose alkali metal salts show an alkaline reaction and they are in any case those which are free of nitrogen, halogen, sulphur and other elements are considered hydrogenation catalyst poisons. Alcoholates are for example those of methanol, ethanol, propanol, butanol and of other alcohols.

The active materials mentioned of the catalysts according to the invention are disposed on a support. Examples of such supports are aluminum oxide, aluminum spinel, activated carbon, kieselguhr, bentonite, pumice, silica gel, $ZrO_2$, $TiO_2$, ZnO, MgO and also oxides of rare earths.

The catalysts according to the invention are preferably disposed on a support made of $Al_2O_3$ or an aluminum spinel. Examples of $Al_2O_3$ are in particular the α-and γ-modifications. Aluminium spinels are compounds of the formula

in which

Me(II) is a divalent metal cation of iron, zinc, nickel, copper, cobalt, cadmium, magnesium or others, preferably of magnesium, and Me(I) is a monovalent cation, for example lithium (lithium/aluminium spinel). The aluminium in the spinels can be replaced in part by trivalent iron, chromium or manganese.

The catalysts according to the invention can be prepared by applying the noble metals mentioned in the form of suitable salts and also the alkaline alkali metal compounds in separate processes to one of the supports mentioned, preferably to an $Al_2O_3$ or an aluminum spinel in the form of extrudates, pills or balls having dimensions of about 2-10 mm and drying them after each separate application. The drying is carried out in a known manner, for example at 100°-140° C. and reduced to atmospheric pressure, for example at 1-1000 mbar, often 10-500 mbar, for example at an aspirator vacuum. Preferably, this application is carried out by means of aqueous solutions. However, as a rule, alcoholic solutions or solutions in lower carboxylic acids or lower amines can also be used, provided the intended salts of the noble metals or the basic alkali metal compounds are soluble therein.

Examples of suitable salts of the noble metals are the chlorides, nitrates, acetates. Irrespective of whether the application of the alkaline alkali metal compounds is carried out before or after the application of the noble metal salts, the noble metals are precipitated in the form of their oxides or hydroxides on the support as soon as they are brought into contact with the alkaline alkali metal compounds. After a final drying operation, the catalyst according to the invention is ready for use.

Before being used, it is preferably activated in a reactor by treating it with hydrogen at an elevated temperature, such as 120°–400° C., preferably at 150°–380° C.

The catalysts according to the invention can be used for the ring hydrogenation of aniline in a highly advantageous manner. Surprisingly, this hydrogenation can be carried out in a gas phase reaction at reduced pressure, atmospheric pressure or only slightly elevated pressure, that is, virtually in the absence of pressure. Therefore, the mechanical requirements of the industrial apparatuses required and thus the price of manufacturing can be significantly reduced. Furthermore, the mixture of cyclohexylamine and dicyclohexylamine being formed in the ring hydrogenation of aniline can be surprisingly controlled in its ratio to one another by the selection of the reaction temperature.

Accordingly, the invention furthermore relates to a process for the preparation of a mixture of substituted or unsubstituted cyclohexylamine and substituted or unsubstituted dicyclohexylamine by hydrogenation of substituted or unsubstituted aniline in the presence of a ruthenium catalyst, which is characterized in that a catalyst containing ruthenium and palladium is used on a support containing the noble metals in a total amount of 0.05–5% by weight and in a weight ratio of ruthenium to other platinum metals such as 1:9–9:1 and furthermore containing 0.1–10% by weight of an alkaline alkali metal compound, all percentages being based on the total weight of the catalyst, and the hydrogenation is carried out at 150° to 220° C. and a pressure of 0.5–10 bar, preferably 0.5 to 4 bar, particularly preferably 0.7 to 2 bar.

In the context of this process according to the invention, the dicyclohexylamine percentage is increased by choosing a lower temperature within the range mentioned.

Furthermore, in a manner known to one skilled in the art the lower region of the entire temperature range is predominantly correlated with lower pressures in the range mentioned and vice versa.

In the process according to the invention, the space velocity of the catalyst is set to 0.05–2 kg, preferably 0.1–0.5 kg of aniline per litre of catalyst and per hour.

A small change in the dicyclohexylamine percentage obtained, for example through changed activity of the catalyst over longer reaction periods, can be balanced by a small adjustment of the reaction temperature or the other parameters mentioned. The desired ratio of cyclohexylamine to dicyclohexylamine can be monitored in a simple manner by analysing the reaction mixture.

Suitable starting materials with respect to the following reaction equation are aniline and substituted anilines, which are converted to the corresponding cyclohexylamines and dicyclohexylamines:

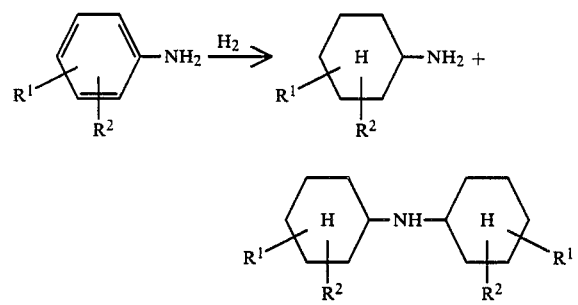

The radicals $R^1$ and $R^2$ independently of one another denote hydrogen, $C_1$-$C_4$-alkyl or $C_1$-$C_4$-alkoxy. Examples of the alkyl and alkoxy substituents mentioned are: methyl, ethyl, propyl, isopropyl, butyl, isobutyl, methoxy, ethoxy, propoxy, isopropoxy, butoxy or isobutoxy. Preferably, the substituents mentioned have 1–2 C atoms, particularly preferably they are methyl or methoxy. In a further preferred manner, one of the substituents $R^1$ and $R^2$ denotes hydrogen, while the other substituent denotes alkyl or alkoxy of the type defined. In a particularly preferred manner, the process according to the invention is aimed at the ring hydrogenation of unsubstituted aniline.

In the process according to the invention, 1–100 litres of hydrogen, preferably 1–50 litres of $H_2$, under standard conditions are used per 1 g of aniline.

Cyclohexylamines and dicyclohexylamines of the type defined are used for the preparation of anti-ageing agents for synthetic rubbers and plastics, as anticorrosives and also as precursors for plant-protection agents and textile aids.

The process according to the invention, which can be carried out in the low pressure range, for the preparation of a mixture of substituted or unsubstituted cyclohexylamine and substituted or unsubstituted dicyclohexylamine is furthermore highly suitable for the direct combination with a process, which can also be carried out in the low pressure range, for the preparation of substituted or unsubstituted diphenylamine from the substituted or unsubstituted dicyclohexylamines, which can be prepared according to the invention.

This process for the preparation of diphenylamine can be carried out at 250°–450° C. and at a pressure of 1–10 bar, the catalyst used being one containing rhodium and at least one other platinum metal from the group consisting of palladium, platinum and iridium, which metals are disposed on a support from the group consisting of $Al_2O_3$ and aluminium spinel, which had been treated with chromium and manganese. Such a catalyst contains the noble metals in a total amount of 0.05–5% by weight, preferably 0.05–4% by weight, particularly preferably 0.1–3% by weight; the percentage by weight of rhodium with respect to the total amount of the noble metals is 10–90%, preferably 15–80%, particularly preferably 20–70%. This catalyst additionally contains additives of 1–6% by weight of an alkali metal hydroxide and 1–6% by weight of an alkali metal sulphate. All percentages mentioned are based on the total weight of the catalyst.

In the combination of the process according to the invention and the last-mentioned process for the preparation of diphenylamine, the mixture obtained according to the invention of substituted or unsubstituted cyclohexylamine and substituted or unsubstituted dicyclohexylamine is used. This mixture to be used can furthermore contain N-cyclohexylanilines. This mixture for the preparation of diphenylamine, which results from the process according to the invention, is brought into contact with the rhodium-containing catalyst mentioned as suitable for the preparation of diphenylamine by means of an inert carrier gas stream, for example an $N_2$ or $H_2$ stream. This makes it possible to utilize the excess hydrogen resulting from the preparation according to the invention of cyclohexylamine and dicyclohexylamine as such a carrier gas.

In a further preferred manner, the stages of the hydrogenation of aniline according to the invention to give the mixture cyclohexylamine/dicyclohexylamine and the stage of preparation of diphenylamine can be combined in terms of apparatuses in such a manner that in a reactor containing two beds connected in series of the ruthenium or rhodium catalysts described above, first aniline is converted in the presence of hydrogen according to the invention and then the resulting mixture is directly further reacted over the second catalyst bed to give diphenylamine. The reaction mixture remaining after the desired diphenylamine has been separated off can be recycled into the process according to the invention in such a recycling. It may be wise to remove by washing or condensing by compression some of the ammonia formed in the hydrogenation of aniline to give the mixture cyclohexylamine/dicyclohexylamine. The principle of such a removal of ammonia is known to one skilled in the art.

EXAMPLE 1

500 g of a commercially available $\gamma$-$Al_2O_3$ having a specific surface area of 350 m$^2$/g and a spherical diameter of 2 to 6 mm were impregnated with a solution which had been prepared from 20 g of NaOH and 170 g of water. The impregnated $Al_2O_3$ was dried at 120° C. in an aspirator vacuum. 100 g of the $Al_2O_3$ thus treated were impregnated with a solution which had been prepared from 1.50 g of $RuCl_3$, 1.17 g of $PdCl_2$ and 30 g of water. 30 ml (23.1 g) of the catalyst again dried at 120° C. in an aspirator vacuum were activated in a hydrogen stream of 10 l/h at 200° C. for 24 hours. 4.07 g of aniline together with 20 l of hydrogen were passed per hour through this catalyst which was present in a vertically arranged 17 mm wide reaction tube. During the duration of the experiment of more than 4000 hours, the reaction temperature was varied between 160 and 200° C. The resulting reaction product was condensed and analyzed at various intervals. The following composition of the reaction product as a function of the time on stream of the catalyst and the reaction temperature was found:

| Duration of the experiment: | 612h | 3043h | 3272h | 4175h |
|---|---|---|---|---|
| Cyclohexylamine | 19.3 | 21.6 | 20.5 | 17.2% |
| Dicyclohexylamine | 80.3 | 66.8 | 76.2 | 81.9% |
| N-cyclohexylaniline | 0.1 | 2.0 | 0.8 | —% |
| Aniline | 0.1 | 9.3 | 2.4 | 0.8% |
| Byproducts | 0.2 | 0.3 | 0.1 | 0.1% |
| Reaction temperature | 160 | 200 | 180 | 160° C. |

EXAMPLE 2

In this example, aniline served as the starting compound for the preparation of diphenylamine. For this experiment, two reaction tubes (internal diameter=17 mm) on top of one another, each of which was charged with different catalysts and maintained at different temperatures, were used. In the first (upper) reaction tube, 30 ml of a catalyst consisting of Ru (0.5%) and Pd (0.5%) on $Al_2O_3$, to which 4% strength NaOH had been added, were present.

This catalyst bed was kept at 180° C.

This catalyst had been prepared as follows:

500 g of a commercially available $\gamma$-$Al_2O_3$ (spherical diameter: 2–5 mm) having a specific surface area of 350 m$^2$/g were impregnated with a solution of 20 g of NaOH in 170 ml of water and subsequently dried. 100 g of the $Al_2O_3$ thus treated were impregnated with a solution of 2.5 g of $RuCl_3$ and 0.83 g of $PdCl_2$ in 30 ml of water, then dried at 120° C. and then activated in a hydrogen stream at 250° C. for 2 hours.

The reaction tube containing the catalyst thus prepared was connected to a second tube in which 30 ml of a catalyst were present, which had been prepared as follows: 50 g of a $\gamma$-$Al_2O_3$ to which chromium and manganese had been applied according to European Patent Application No. 0,208,933, Example 1, were uniformly impregnated in a round-bottom flask with a solution of 0.66 g of $RhCl_3$ and 0.83 g of $H_2PtCl_6$ in 15 ml of water. The moist catalyst pellets were dried at 120° C. and then impregnated again with a solution of 1.46 g of NaOH in 15 ml of water and dried again. The pellets were then impregnated again with a solution of 1.5 g of $K_2SO_4$ in 15 ml of water and dried again. This catalyst was maintained at a temperature of 380° C. 90 g of aniline together with 10 l of $H_2$/h were passed into the reaction tubes thus connected in series over a period of 21.5 h. The reaction product leaving the second reaction tube was condensed and analyzed. Analysis showed the following composition:

| | |
|---|---|
| Diphenylamine: | 60.4% |
| Cyclohexylamine: | 0.4% |
| N-cyclohexylaniline: | 6.3% |
| Aniline: | 32.3% |
| Byproducts: | Balance |

The mixture remaining after the diphenylamine had been separated off was recycled.

The uncondensed flue gas was also recycled, after some of the $NH_3$ had been removed.

EXAMPLE 3

200 g of a commercially available $\gamma$-$Al_2O_3$ having a specific surface area of 350 m$^2$/g and a spherical diameter of 2–6 mm were impregnated with a solution which had been prepared from 3.0 g $RuCl_3$ and 49 g of water. The catalyst support thus impregnated was dried at 120° c. in an aspirator vacuum and subsequently reduced in a hydrogen stream at 350° C. for 3 hours. The catalyst was then impregnated with a solution which had been prepared from 8 g of NaOH and 49 g of water.

40 ml (32.6 g) of the catalyst dried at 120° C. in an aspirator vacuum were used for the hydrogenation of aniline in the gas phase. 4.22 g of aniline together with 20 l of $H_2$ were passed per hour through the catalyst bed at 180° C. The reaction product produced after 324 hours had the composition listed in column A:

| | A | B |
|---|---|---|
| Cyclohexylamine | 16.7 | 35.0 |
| Dicyclohexylamine | 0.9 | 63.8 |
| N-cyclohexylaniline | 5.9 | 0.6 |
| Aniline | 75.9 | 0.3 |
| Byproducts | 0.6 | 0.3 |

The product composition listed in column B, on the other hand, was obtained by using 40 ml (32.6 g) of a catalyst which had been prepared in an exactly identical manner, except that it contained a combination of Ru with Pd. It was prepared by impregnating 200 g of the same $Al_2O_3$ with an aqueous solution containing 2.35 g of $PdCl_2$ and 3.0 g of $RuCl_2$. The further procedure of preparing the catalyst was exactly identical to that of the Ru catalyst, which was used first and gave the hydrogenation result listed in A.

What is claimed is:

1. A process for the preparation of a mixture of a substituted or unsubstituted cyclohexylamine and a substituted or unsubstituted dicyclohexylamine by hydrogenation of a substituted or unsubstituted aniline in the presence of a ruthenium catalyst, wherein the catalyst comprises ruthenium and palladium on a support containing the noble metals in a total amount of 0.05–5% by weight and a weight ratio of ruthenium to palladium such as 1:9–9:1 and furthermore containing 0.1–10% by weight of an alkaline alkali metal compound, all percentages being based on the total weight of the catalyst, said hydrogenation being carried out at 150°–220° C. and at a pressure of 0.5–10 bar.

2. The process of claim 1, wherein to increase the percentage of dicyclohexylamine the hydrogenation is carried out at a lower temperature within the range of 150°–220° C.

3. The process of claim 1, wherein the space velocity of the catalyst is set to 0.5–2 kg of aniline per liter of catalyst and per hour.

4. The process of claim 1, wherein the aniline is of the formula

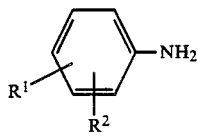

in which
R¹ and R² independently of one another denote hydrogen, $C_1$–$C_4$-alkyl or $C_1$–$C_4$-alkoxy.

5. The process of claim 1 wherein 1–100 liters of hydrogen under standard conditions are used per 1 g of the aniline.

6. The process of claim 1, wherein the hydrogenation is carried out in the gas phase.

7. A process according to claim 1, wherein the noble metals are present in a total amount of 0.1–4% by weight.

8. A process according to claim 1, wherein the noble metals are present in a total amount of 0.1–3% by weight.

9. A process according to claim 1, wherein the noble metals are present in a weight ratio of ruthenium to palladium 2:8–8:2.

10. A process according to claim 1, wherein the noble metals are present in a weight ratio of ruthenium to palladium such as 3:7–7:3.

11. A process according to claim 1, wherein the catalyst contains 0.2–5% by weight of a basic alkali metal compound.

12. A process according to claim 1, wherein the support is $Al_2O_3$ or an aluminum spinel.

13. A process according to claim 1, wherein, prior to its use, the catalyst is treated with hydrogen at 120°–400° C.

14. A process according to claim 13, wherein, prior to its use, the catalyst is treated with hydrogen at 150°–380° C.

15. A process according to claim 1 wherein the alkaline alkali metal compounds are the oxides, hydroxides, alcoholates or salts of weak acids of lithium, sodium, potassium, rubidium or caesium.

16. A process according to claim 15, wherein the alkaline alkali metal compounds are the oxides, hydroxides, alcoholates or salts of weak acids of sodium or potassium.

17. A process according to claim 1, wherein the catalyst support is aluminum oxide, aluminum spinel, activated carbon, kieselgur, bentonite, pumice, silica gel, $ZrO_2$, $TiO_2$, ZnO, MgO or an oxide of rare earths.

* * * * *

UNITED STATES PATENT AND TRADEMARK OFFICE
CERTIFICATE OF CORRECTION

PATENT NO. : 4,952,549

DATED : August 28, 1990

INVENTOR(S) : Immel et al.

It is certified that error appears in the above-identified patent and that said Letters Patent is hereby corrected as shown below:

Title Page     U.S. PATENT DOCUMENTS: After " 3,697,449, 10/1972 " delete " Loren " and substitute -- Brake --

Signed and Sealed this

Twenty-fifth Day of August, 1992

Attest:

DOUGLAS B. COMER

Attesting Officer     Acting Commissioner of Patents and Trademarks

UNITED STATES PATENT AND TRADEMARK OFFICE
CERTIFICATE OF CORRECTION

PATENT NO. : 4,952,549

DATED : August 28, 1990

INVENTOR(S) : Immel et al.

It is certified that error appears in the above-identified patent and that said Letters Patent is hereby corrected as shown below:

Title Page    ABSTRACT:    Lines 1 & 2 delete " substituted or substituted " and substitute -- substituted or unsubstituted --

Signed and Sealed this

Sixteenth Day of November, 1993

Attest:

BRUCE LEHMAN

*Attesting Officer*      *Commissioner of Patents and Trademarks*